(12) United States Patent
Green et al.

(10) Patent No.: US 6,422,997 B1
(45) Date of Patent: Jul. 23, 2002

(54) PROSTATE VISUALIZATION DEVICE AND METHODS OF USE

(75) Inventors: Thomas C. Green, Seattle, WA (US); Michael J. Horzewski, San Jose, CA (US)

(73) Assignee: Neoseed Technology LLC, San Francisco, CA (US)

( * ) Notice: Subject to any disclaimer, the term of this patent is extended or adjusted under 35 U.S.C. 154(b) by 59 days.

(21) Appl. No.: 09/648,319

(22) Filed: Aug. 25, 2000

(51) Int. Cl.[7] ............................ A61B 1/32; A61B 8/14; A61M 29/00; A61N 5/00
(52) U.S. Cl. ................... 600/207; 604/101.03; 600/3; 600/437
(58) Field of Search ............................ 600/204, 3, 437, 600/207; 604/101.03, 96, 49, 508, 103.1, 509; 606/108, 48, 15, 192; 607/99

(56) References Cited

U.S. PATENT DOCUMENTS

| | | | |
|---|---|---|---|
| 4,700,692 A | 10/1987 | Baumgartner | |
| 5,188,596 A | * 2/1993 | Condon et al. | 604/103.1 |
| 5,209,725 A | * 5/1993 | Roth | 604/508 |
| 5,301,688 A | * 4/1994 | Stepjem et al. | 607/99 |
| 5,409,483 A | * 4/1995 | Campbell et al. | 606/15 |
| 5,458,612 A | * 10/1995 | Chin | 606/192 |
| 5,626,829 A | 5/1997 | Koutrouvelis | |
| 5,628,746 A | * 5/1997 | Clayman | 606/45 |
| 5,715,825 A | 2/1998 | Crowley | |
| 5,855,563 A | * 1/1999 | Kaplan et al. | 604/49 |
| 5,865,728 A | * 2/1999 | Moll et al. | 600/204 |
| 5,868,778 A | 2/1999 | Gershony et al. | |
| 5,871,448 A | 2/1999 | Ellard | |
| 5,876,417 A | * 3/1999 | Devonec et al. | 606/192 |
| 5,899,882 A | * 5/1999 | Waksman et al. | 604/96 |
| 5,916,153 A | 6/1999 | Rhea, Jr. | |
| 5,928,130 A | 7/1999 | Schmidt | |
| 5,938,583 A | 8/1999 | Grimm | |
| 6,033,413 A | * 3/2000 | Mikus et al. | 606/108 |
| 6,036,631 A | 3/2000 | McGrath et al. | |
| 6,083,166 A | 7/2000 | Holdaway et al. | |
| 6,299,598 B1 | * 10/2001 | Bander | 604/101.03 |

* cited by examiner

*Primary Examiner*—Eric F. Winakur
*Assistant Examiner*—Nikita R Veniaminov
(74) *Attorney, Agent, or Firm*—Fish & Neave; Nicola A. Pisano (57) ABSTRACT

Methods and apparatus are provided for improved administration of brachytherapy in the treatment of prostate disease. More particularly, a prostate visualization device is provided comprising a disk-shaped bladder neck balloon that sealing engages and defines an enclosed space within a proximal region of a patient's bladder. The device is preferably coupled to a catheter for injection of echo-contrast agent into the enclosed space to facilitate imaging of the patient's bladder/prostate junction with an ultrasound system. The device may alternatively be radiopaque. Apparatus for selectively stiffening the catheter is also provided.

60 Claims, 6 Drawing Sheets

PROSTATE VISUALIZATION DEVICE AND METHODS OF USE

FIELD OF THE INVENTION

This invention relates to improved apparatus and methods for the treatment of prostate cancer. More particularly, the present invention provides a prostate visualization device comprising a bladder neck balloon, and methods of use.

BACKGROUND OF THE INVENTION

Excluding nonmelanoma skin cancers, prostate cancer is the most common cancer afflicting American men. The American Cancer Society estimates that over 180,00 new cases will be diagnosed in the U.S. in the year 2000 alone, and that nearly 32,000 people will die from the disease. Prostate cancer is second only to lung cancer as the leading cause of cancer death in men, accounting for roughly 11%.

Prostate cancer is defined as malignant tumor growth within the prostate gland. Its cause is unknown, although high dietary fat intake and increased testosterone levels are believed to be contributory factors. A letter scale ("A" through "D"), which accounts for the location of the cancer, is commonly used to classify the stage of disease. In Stage A, the tumor is not palpable but is detectable in microscopic biopsy. Stage B is characterized by a palpable tumor confined to the prostate. By Stage C, the tumor extends locally beyond the prostate with no distant metastasis. By Stage D, cancer has spread to the regional lymph nodes or has produced distant metastasis.

In the early stages, prostate cancer is most commonly treated by either prostate removal or by brachytherapy. More advanced cases are treated by hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been developed and holds great promise for the treatment of early stage prostate cancer. Radioactive pellets or seeds of, for example, iodine-125, palladium-103, or iridium-192, are deposited directly into the prostate through needle placement. U.S. Pat. No. 5,928,130 to Schmidt provides a slightly modified example of such a needle device. Imaging techniques, such as transrectal ultrasound, CT scans, or MRI, are used to accurately guide placement of the radioactive material. Advantageously, radiation from the brachytherapy seeds is administered directly to the prostate with less damage to surrounding tissues, delivering a substantially higher radiation dosage to the prostate than to the surrounding tissues, as compared to external beam radiation therapy. The procedure need only be performed once, and impotence and urinary incontinence complications are significantly reduced, as compared to prostate removal procedures.

The seeds, which are permanently implanted, give off radiation for weeks or months. Their presence causes little discomfort, and they remain in the prostate after decay of the radioactivity. For several weeks following needle insertion, patients may experience pain in the perineal area, and urine may have a red-brown discoloration.

Although, when performed correctly, brachytherapy may provide several benefits when compared to prostate removal and other techniques, current surgical apparatus and methods for delivering the seeds to target locations within the prostate are somewhat crude and are subject to practitioner error. The current method of identifying the depth of needle insertion is by ultrasound imaging. The junction of the base of the prostate and the bladder provides a common reference plane for needle insertion. Identifying this critical reference "base" plane is critical to proper needle and seed placement.

A present technique for imaging the base plane is to visualize the plane in either transverse or sagittal ultrasound imaging. Injection of contrast agent may facilitate imaging. A catheter, such as a standard Foley catheter, may be inserted into the patient's urethra proximal of the junction. Contrast agent comprising aerated K-Y jelly and water, may then be injected through an end port of the catheter. The agent moves distally towards the patient's bladder and is visible to an ultrasound probe, positioned in the patient's rectum, thereby facilitating imaging.

Attempts have been made to improve Foley catheters, as well as to facilitate improved imaging within a body lumen. For example, U.S. Pat. No. 5,715,825 to Crowley provides an acoustic imaging catheter with an inflatable dilation balloon and an ultrasound transducer. However, while Crowley may provide improved imaging, the device is mechanically and electrically complex, and is therefore subject to failure. U.S. Pat. No. 5,916,153 to Rhea, Jr. provides a multifunction, modified Foley catheter. The device described in that patent, however, does nothing to improve on current junction imaging techniques.

Progress has been made in the field of vascular wound closure in creating devices that conform to the shape of a vascular puncture to facilitate sealing of the puncture. For example, U.S. Pat. No. 5,868,778 to Gershony et al. provides a vascular sealing device with a balloon positioned at an end region. The device is inserted through a vascular puncture, the balloon is inflated, and the device is retracted until the balloon seals against the puncture.

In view of the drawbacks associated with previously-known methods and apparatus for bladder/prostate junction imaging, it would be desirable to provide methods and apparatus that overcome such drawbacks.

It further would be desirable to provide methods and apparatus that provide uniform and reliable imaging of the junction.

It still further would be desirable to provide methods and apparatus that may be used in conjunction with standard brachytherapy apparatus.

SUMMARY OF THE INVENTION

In view of the foregoing, it is an object of the present invention to provide methods and apparatus for bladder/prostate junction imaging that overcome drawbacks associated with previously-known methods and apparatus.

It is also an object of the present invention to provide methods and apparatus that provide uniform and reliable imaging of the bladder/prostate junction.

It still further is an object to provide methods and apparatus that may be used in conjunction with standard brachytherapy apparatus.

These and other objects of the present invention are accomplished by providing methods and apparatus for bladder/prostate junction imaging comprising a bladder neck balloon that sealing engages and defines an enclosed space within a proximal region of the bladder. The balloon may, for example, be shaped such that it conforms to the proximal region when inflated, or it may comprise regions of reduced elasticity such that it expands nonuniformly into the required shape. Echo-contrast agent may be injected into the enclosed space with uniform density, to facilitate reliable imaging with an ultrasound probe. Alternatively, the bladder neck balloon may be fabricated from a material that is opaque to ultrasound, thereby negating the need for contrast agent.

In a preferred embodiment, the balloon is coupled to a multi-lumen catheter. The lumens include an inflation lumen, a bladder drainage lumen, a contrast lumen, and a prostatic therapy lumen. The catheter is advanced through a patient's urethra into the patient's bladder. The balloon is inflated via the inflation lumen, and the catheter is proximally retracted until the balloon sealingly engages the proximal region and defines the enclosed space. Echo-contrast agent is injected into the space through the contrast lumen, such that it fills the space. Ultrasonic imaging may then proceed, often with an ultrasound probe positioned in the patient's rectum. Urine may also be emptied from the bladder via the bladder drainage lumen, and the patient's prostate may be accessed via the prostatic therapy lumen.

In an alternative embodiment with a radiopaque balloon, the catheter optionally may be provided without the contrast lumen. With the balloon sealingly engaging the proximal region and defining the enclosed space, ultrasonic imaging proceeds.

The bladder neck balloon may comprise a variety of shapes to facilitate imaging of bladders of different shapes and sizes. Shapes suited to specific patient populations will be apparent to those of skill in the art, and fall within the scope of the present invention.

Methods of using the present invention are also provided.

BRIEF DESCRIPTION OF THE DRAWINGS

Additional objects and advantages of the invention will be apparent from the following description, the appended claims, and the accompanying drawings, in which like reference characters refer to like parts throughout, and in which:

DETAILED DESCRIPTION OF THE INVENTION

The present invention provides methods and apparatus for improved administration of brachytherapy. More particularly, the present invention provides a prostate visualization device comprising a bladder neck balloon that sealing engages and defines an enclosed space within a proximal region of a patient's bladder. The device is preferably coupled to a catheter to facilitate imaging of the patient's bladder/prostate junction.

Figure 1:
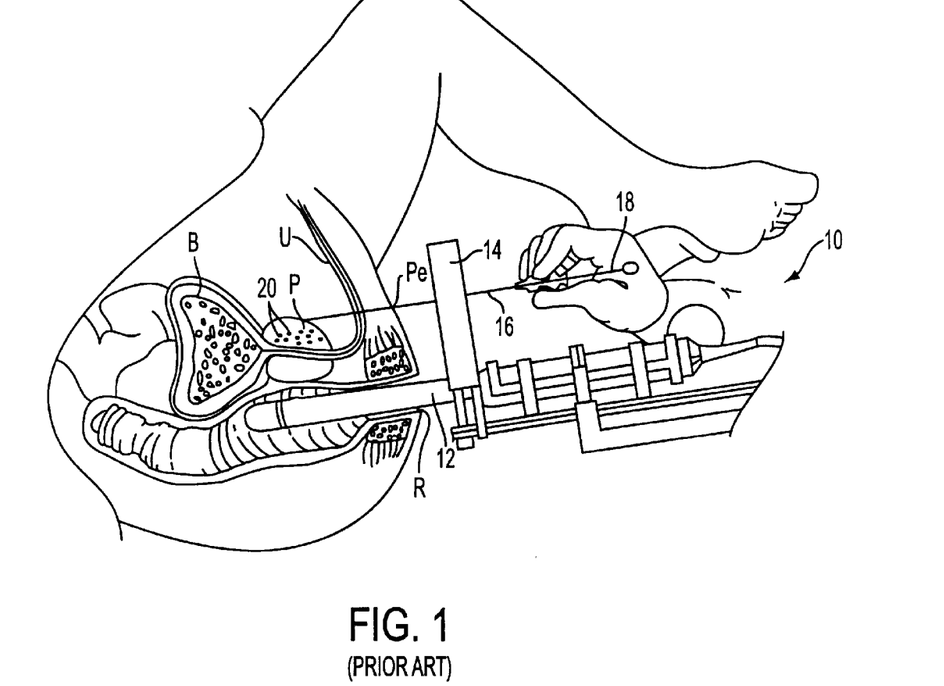
FIG. 1 is a schematic view of a prior art method of performing brachytherapy.
Figure 2:
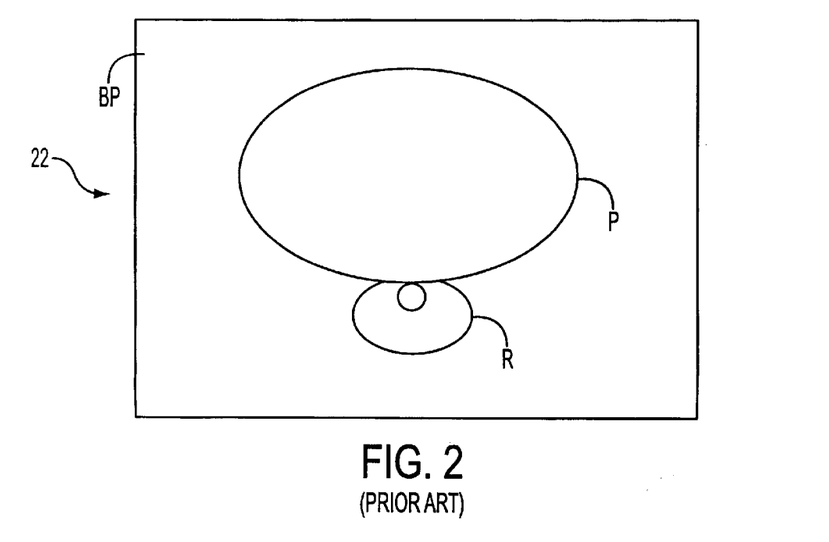
FIG. 2 is a schematic view detailing the prior art method of imaging the bladder/prostate junction in greater detail.

Referring now to FIGS. 1 and 2, a prior art method of performing brachytherapy is described. The method and apparatus are as taught by Peter Grimm, DO, in a pamphlet entitled, "Ultrasound Guided Implantation of the Prostate: A Practical Review Course." As seen in FIG. 1, brachytherapy apparatus 10 comprises transrectal ultrasound probe 12, guide block 14, needle 16, plunger 18, and radioactive seeds 20. Ultrasound probe 12 is advanced through a patient's rectum R to facilitate imaging of the patient's prostate P. Prostate P surrounds urethra U and is just proximal of bladder B. An ultrasonic image of a junction between the prostate and the bladder is acquired, as described hereinbelow with respect to FIG. 2. Needle 16, loaded with seeds 20 and plunger 18, is then advanced through guide block 14, through the patient's perineum Pe, and into prostate P, where needle 16 is retracted while plunger 18 is held stationary to sew the seeds in a line within prostate P.

With reference to FIG. 2, the imaging aspect of the apparatus and method of FIG. 1 is described in greater detail. A catheter, such as a standard Foley catheter, is inserted into the patient's urethra proximal of the patient's bladder/prostate junction. A combination of water and KY jelly is then injected through an end port of the catheter. The combination moves distally towards the patient's bladder and appears to ultrasound probe 12 as contrast agent. Ultrasound probe 12 then provides signals that are converted by a previously known ultrasound system to display ultrasonic image 22 of base plane BP, which is located tangent to the distal surface of prostate P, i.e. at the prostate/bladder junction. All positions within the prostate are determined relative to base plane BP during the brachytherapy procedure.

Ultrasonic imaging and location determination of base plane BP may be unreliable due to irregular ultrasonic images dependent on a density of the water/KY jelly combination at a given location, as well as flow conditions within the bladder and urethra. Thus, there exists a need for reliable apparatus and methods for bladder/prostate junction imaging.

Figure 3A:
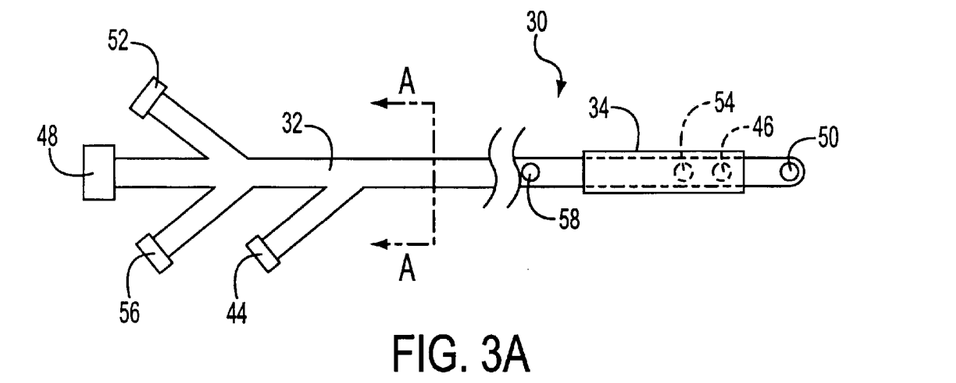
FIGS. 3A–3C are, respectively, a side view of apparatus constructed in accordance with the present invention in a collapsed delivery state, a sectional view of the apparatus through section line A—A of FIG. 3A, and a side view, partly in section, of the apparatus in an expanded deployed state.
Figure 3B:
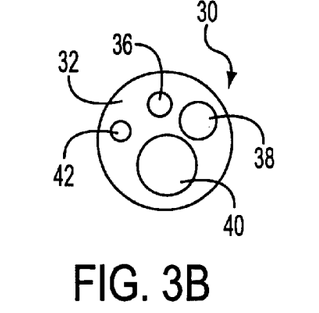
Figure 3C:
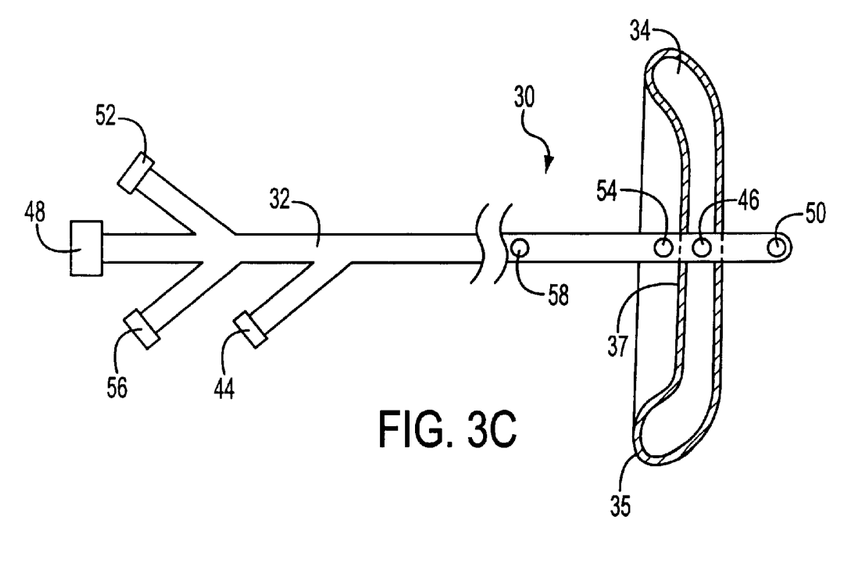

With reference now to FIG. 3, a first embodiment of apparatus constructed in accordance with the present invention is described. Apparatus 30 comprises catheter 32 coupled to disk-like bladder neck balloon 34. Catheter 32 further comprises inflation lumen 36, bladder drainage lumen 38, contrast lumen 40, and prostatic therapy lumen 42. Bladder neck balloon 34 preferably is slightly concave, with its outer edge 35 being displaced proximally relative to its center 37, where it attaches to catheter 32.

Inflation lumen 36 extends between proximal inflation port 44 and distal inflation port 46, which is coupled to bladder neck balloon 34. Drainage lumen 38 extends between proximal drainage port 48 and distal drainage port 50, which is located distal of balloon 34. Contrast lumen 40 extends between proximal contrast port 52 and distal contrast port 54, which is located just proximal of distal inflation port 46. Prostatic therapy lumen 42 extends between proximal prostate port 56 and distal prostate port 58, which is configured to align with the patient's prostate when balloon 34 engages the patient's bladder. Distal prostate port 58 is preferably positioned 3–5 cm proximal of distal inflation port 46. The exact distance is dependent on the shape and stiffness of balloon 34, as well as the patient's anatomy. Catheter 32 preferably comprises a total length of 35–45 cm, and even more preferably a length of approximately 40 cm.

Bladder neck balloon 34 is expandable from a collapsed delivery configuration seen in FIG. 3A to an expanded deployed configuration seen in FIG. 3C, in which the balloon sealing engages and defines an enclosed space within a proximal region of a patient's bladder. The balloon is preferably fabricated from bands of silastic or latex polyisoprene. The bands are of varying stiffness, thickness, and/or elasticity to provide a balloon that expands nonuniformly to a specified profile, preferably concave in towards the proximal end of the catheter. Alternatively, balloon 34 may have a thin, disk-like shape, so as to partition the bladder when inflated, and it may be fabricated such that it uniformly expands to the specified profile. The balloon is preferably 4–5 cm across with a 1–3 cm offset from center 37 to edge 35. The offset is even more preferably 2 cm.

Figure 4:
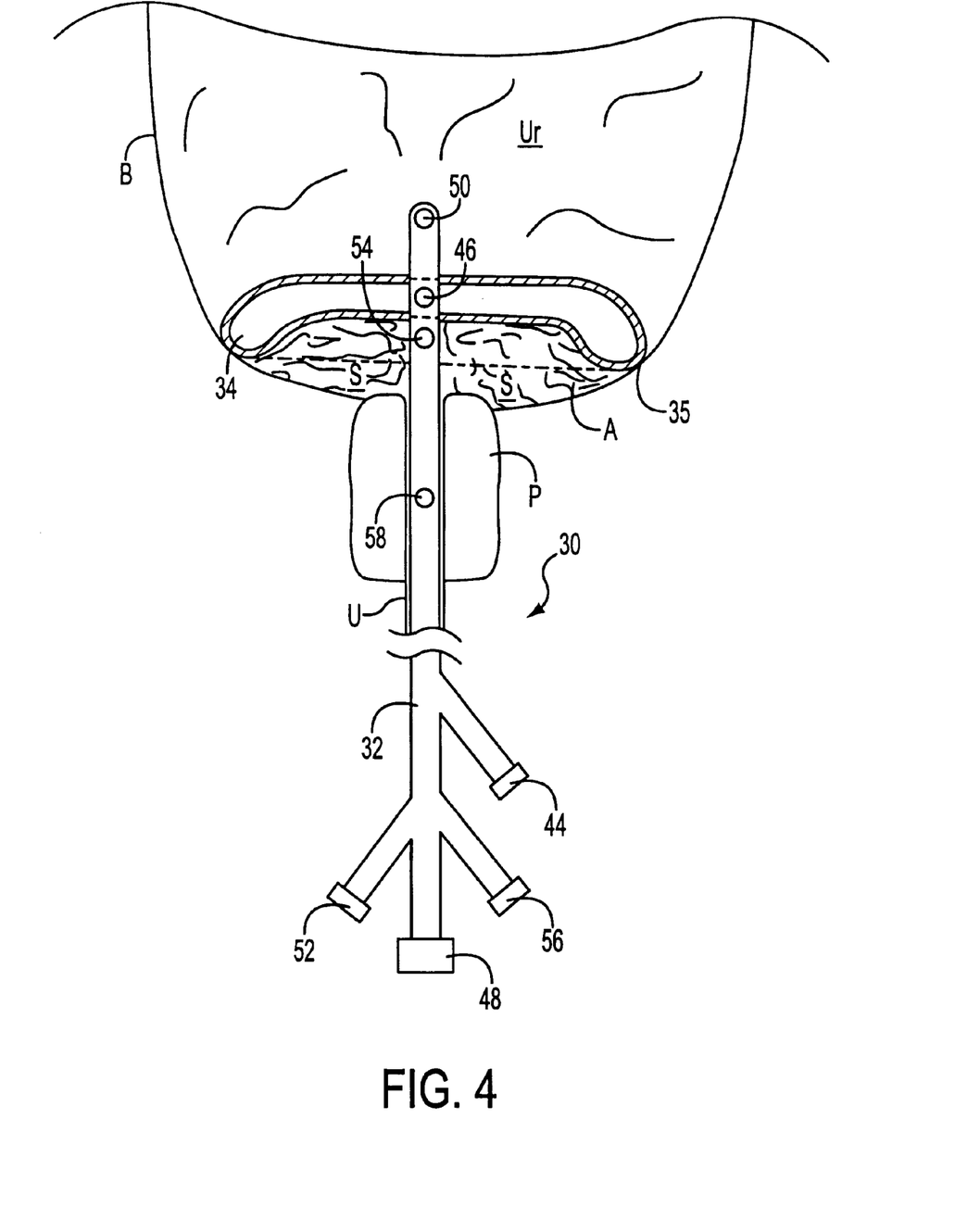
FIG. 4 is a schematic view, partly in cross-section, demonstrating a method of using the apparatus of FIG. 3 to image a patient's bladder/prostate junction.

Referring to FIG. 4, a method of using apparatus 30 in accordance with the principles of the present invention is described. Catheter 32 is advanced through a patient's urethra U into bladder B, with bladder neck balloon 34 in the collapsed delivery configuration. Balloon 34 is then inflated by inflation medium communicated to the balloon through distal inflation port 46, which in turn is coupled via inflation lumen 36 to inflation means (not shown) connected to proximal inflation port 44. With balloon 34 in the expanded deployed configuration, catheter 32 is retracted until bladder neck balloon 34 sealingly engages and defines enclosed space S within a proximal region of bladder B.

Echo-contrast agent A then may be injected into space S. Echo-contrast agent A may, for example, comprise a mixture of water and KY jelly. The agent is injected through proximal contrast port 52, contrast lumen 40, and distal contrast port 54 into enclosed space S. Lumen 40 and ports 52 and 54 preferably are dimensioned in a manner that accounts for the viscosity of the agent. Once agent A has been injected into space S with uniform density, apparatus 30 facilitates reliable ultrasonic imaging with ultrasound probe 12 inserted through the patient's rectum R, as seen in FIG. 1, and provides means for capturing a reliable reference plane, as seen in FIG. 2. The reference plane may be used to conduct or to prepare for brachytherapy treatment of prostate cancer, in the manner discussed hereinabove.

Urine and other fluids Ur may be emptied from the patient's bladder B during and after imaging via bladder drainage lumen 38. Urine Ur enters distal drainage port 50, which is located distal of balloon 34. The urine passes through drainage lumen 38 and out of the patient's body through proximal drainage port 48.

Prostatic therapy lumen 42 provides access to the patient's prostate P. Therapeutic agents or interventional devices may be inserted into lumen 42 through proximal prostate port 56, and deposited into the patient's prostate P via distal prostate port 58. Apparatus 30 thus may be used for a variety of procedures which will be apparent to those of skill in the art and of which brachytherapy is only one example. Upon completion of such a procedure, balloon 34 may be collapsed back to the delivery configuration, and apparatus 30 may be removed from the patient.

Figure 5:
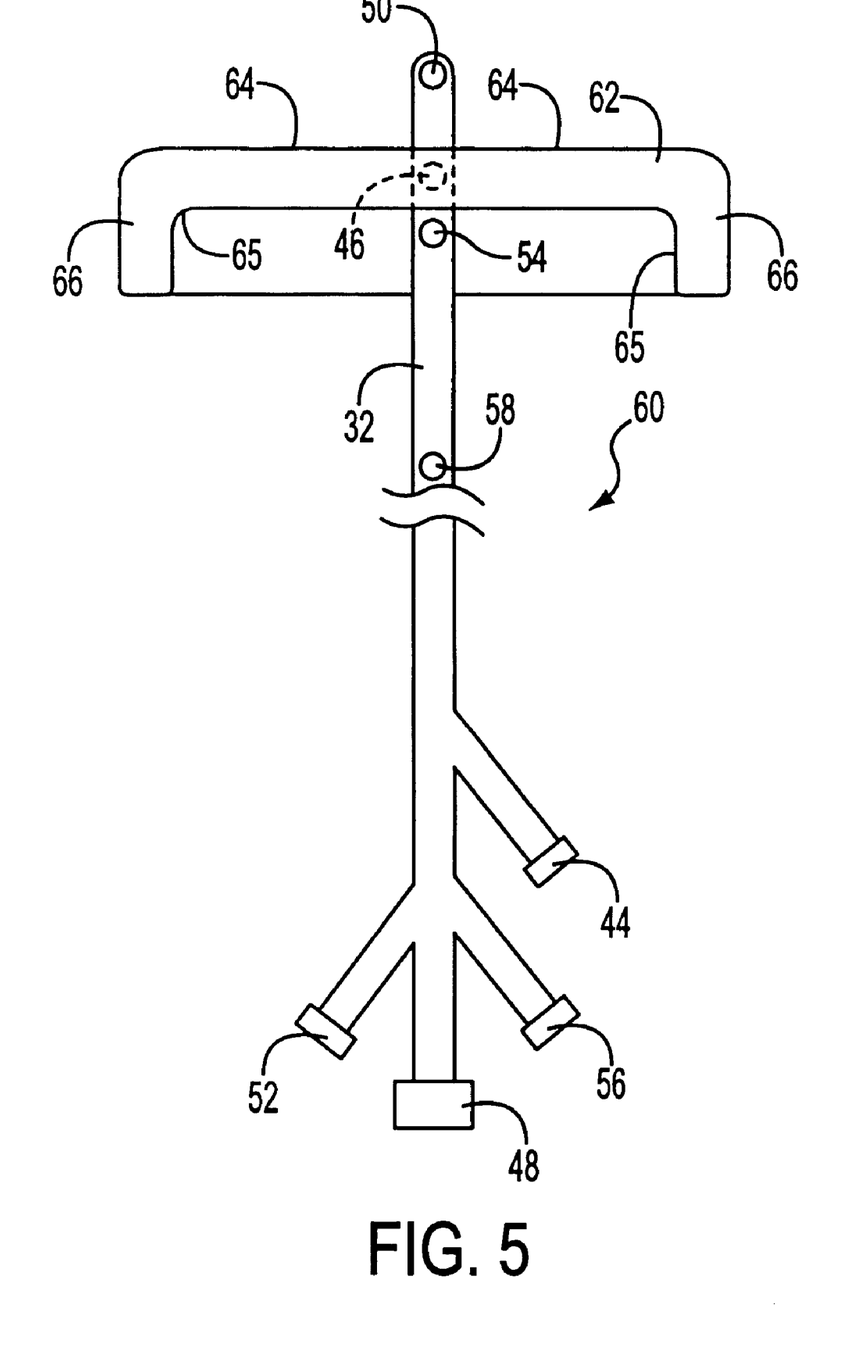
FIG. 5 is a side view of an alternative embodiment of the apparatus of the present invention in an expanded deployed state.

Referring now to FIG. 5, an alternative embodiment of apparatus constructed in accordance with the present invention is disclosed. Apparatus 60 is substantially equivalent to apparatus 30, except for bladder neck balloon 62. Balloon 62 is shown in the expanded deployed configuration and has a different profile than balloon 34. Disk-shaped balloon 62 inflates nonuniformly to a deployed configuration having proximally-directed flange 65. Flange 65 is created by forming disk-shaped portion 64 of a relatively stiff material, with a more elastic material along end section 66. The profile of balloon 62 may provide a larger enclosed space within some patients' bladders and may therefore facilitate improved imaging in those patients.

Figure 6A:
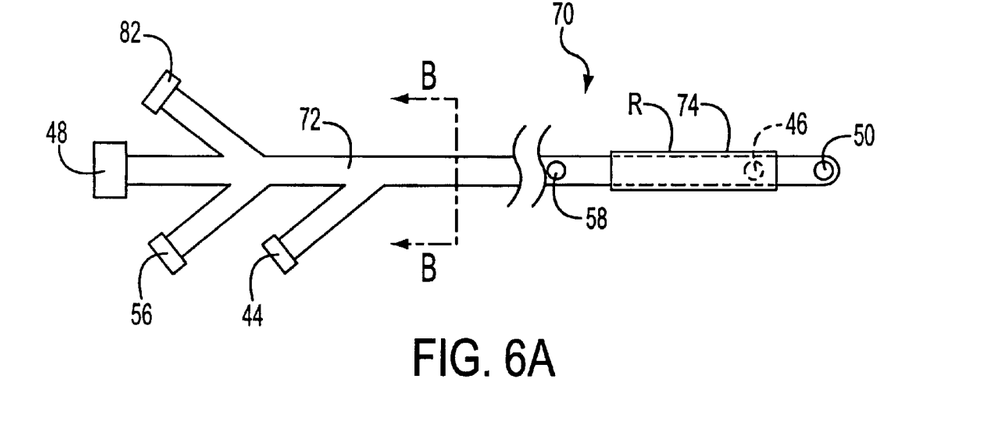
FIGS. 6A–6C are of an alternative embodiment of apparatus of the present invention, shown, respectively, in a collapsed delivery state, in sectional view through section line B—B of FIG. 6A, and in side view, partly in section, in an expanded deployed state.
Figure 6B:
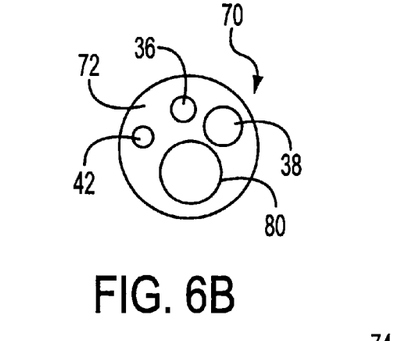
Figure 6C:
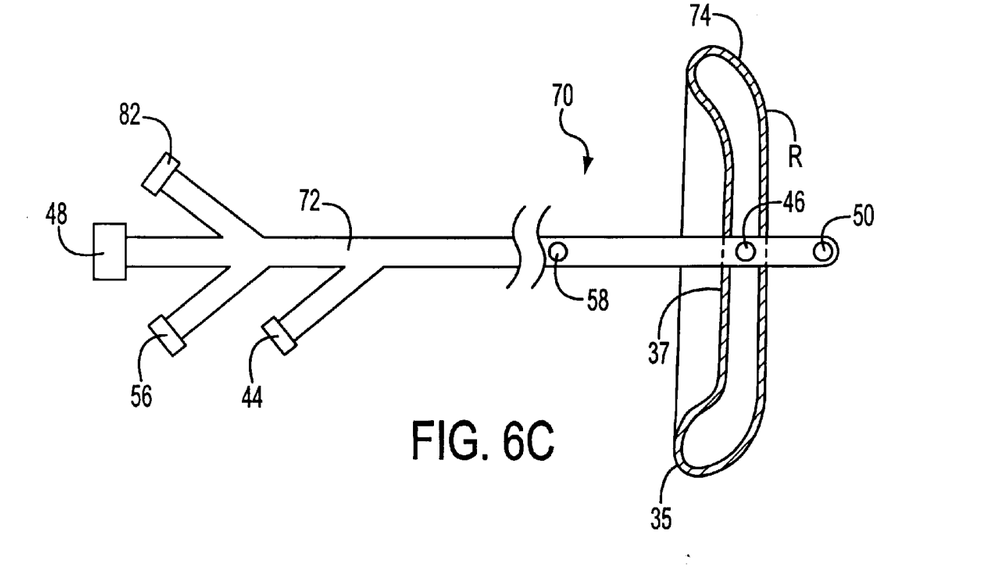

With reference to FIG. 6A–6C, a further alternative embodiment is presented. Apparatus 70 is substantially equivalent to apparatus 30, except that catheter 72 is provided without proximal contrast port 52, distal contrast port 54, or contrast lumen 40, and bladder neck balloon 74 is fabricated from radiopaque material R. The radiopacity of balloon 74 facilitates ultrasonic imaging without injection of echo-contrast agent.

Apparatus 70 of FIG. 6 optionally also may comprise pressure channel 80 coupled to pressure inlet port 82. Channel 80 preferably extends the length of catheter 72. In some cases, a patient's prostate may obstruct advancement of apparatus 70 through the urethra into the bladder. The flexibility of catheter 72 may inhibit passage of apparatus 70 past the obstructing prostate. In such cases, liquid may be injected through port 82 into channel 80, thereby stiffening apparatus 70 to allow passage past the prostate.

Apparatus 70 may further be provided with a natural curve that matches the curve of the urethra when channel 80 is filled. This may be accomplished, for example, by thinning the wall on one side of catheter 72. As will of course be understood, pressure channel 80 could be provided on any of the other apparatus described herein, or on any other catheter wherein selective stiffening would be advantageous, such as a standard Foley catheter.

Figure 7:
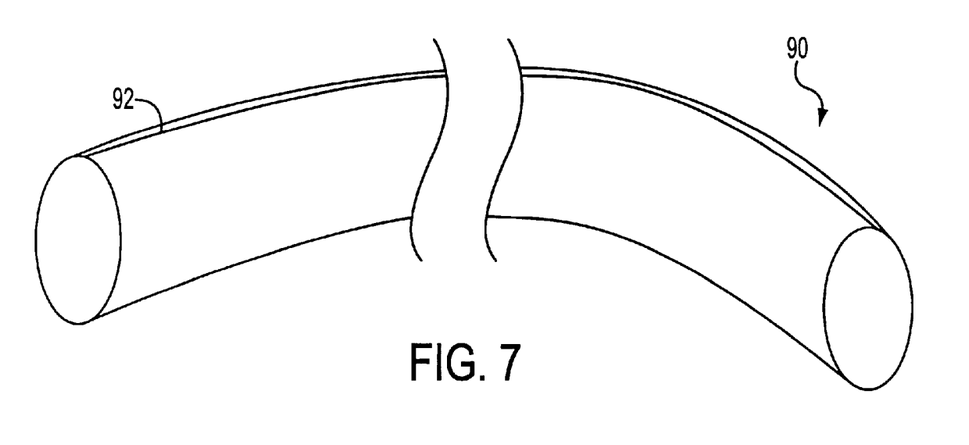
FIG. 7 is an isometric view of a stiffening sleeve in accordance with the present invention.

Referring now to FIG. 7, stiffening may also be accomplished with rigid tubular sleeve 90 that is curved to match the curve of the urethra. Apparatus of the present invention may be coaxially disposed within sleeve 90 during advancement into the bladder. The sleeve then may be removed from both the patient and the apparatus of the present invention by, for example, slipping the apparatus through slit 92 of sleeve 90. In the event that the bladder neck balloon will not deflate, the sleeve may be re-advanced in order to puncture or compress the balloon. As with pressure channel 80 of FIG. 6, sleeve 90 may be used with any apparatus described herein, or on any other catheter wherein selective stiffening would be advantageous, such as a standard Foley catheter.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations, including various alternative balloon shapes, will be apparent to one skilled in the art in light of this disclosure and are intended to fall within the scope of the appended claims.

What is claimed is:

1. Apparatus for facilitating visualization of a patient's prostate comprising:
   a catheter comprising a first inlet port and a first outlet port, a first lumen extending therebetween, and a second inlet port and a second outlet port, a second lumen extending therebetween, the second outlet port disposed proximal of the first outlet port; and
   a disk-shaped bladder neck balloon comprising a proximally-directed flange and coupled to the first outlet port, the balloon expandable from a delivery configuration adapted for transurethral insertion, to a deployed configuration adapted for sealing engagement of an enclosed space within a proximal portion of the patient's bladder.

2. The apparatus of claim 1, wherein the catheter further comprises a third inlet port and a third outlet port, a third lumen extending therebetween, the third outlet port disposed distal of the first outlet port.

3. The apparatus of claim 2, wherein the catheter further comprises a fourth inlet port and a fourth outlet port, a fourth lumen extending therebetween, the fourth outlet port disposed proximal of the second outlet port.

4. The apparatus of claim 1, wherein the catheter further comprises a third inlet port and a third outlet port, a third lumen extending therebetween, the third outlet port disposed proximal of the second outlet port.

5. The apparatus of claim 4, wherein the third outlet port is disposed between 3 cm and 5 cm proximal of the first outlet port.

6. The apparatus of claim 1, wherein the disk-shaped bladder neck balloon is concave towards the proximal end of the catheter in the deployed configuration.

7. The apparatus of claim 1 further comprising:
   brachytherapy apparatus configured for delivery of radioactive seeds to the patient's prostate, wherein delivery of the seeds is facilitated by ultrasonic imaging of a junction of the patient's prostate and bladder.

8. The apparatus of claim 1, wherein the bladder neck balloon is fabricated from a material chosen from the group consisting of silastic and latex polyisoprene.

9. The apparatus of claim 8, wherein the balloon is fabricated from a plurality of bands of the material, the plurality of bands varying each from another by a property chosen from the group consisting of stiffness, thickness, and elasticity.

10. The apparatus of claim 1, wherein the bladder neck balloon is configured to expand nonuniformly to the deployed configuration.

11. The apparatus of claim 1, wherein the bladder neck balloon is configured to expand uniformly to the deployed configuration.

12. The apparatus of claim 1, wherein the catheter has a length of between 35 cm and 45 cm.

13. The apparatus of claim 1, wherein the bladder neck balloon has a diameter of between 4 cm and 5 cm.

14. The apparatus of claim 1, wherein an outer edge of the bladder neck balloon is offset relative to a center of the bladder neck balloon by a distance of between 1 and 3 cm.

15. The apparatus of claim 1 further comprising echo-contrast agent in communication with the second inlet port for delivery of the echo-contrast agent to the enclosed space.

16. The apparatus of claim 1, wherein the bladder neck balloon comprises a radiopaque material.

17. The apparatus of claim 1, wherein the catheter further comprises a pressure channel coupled to a pressure inlet port.

18. The apparatus of claim 1 further comprising a rigid tubular sleeve removably disposed about the catheter.

19. The apparatus of claim 18, wherein the sleeve has a natural curve adapted to match the curve of a patient's urethra.

20. The apparatus of claim 1, wherein the catheter has a natural curve adapted to match the curve of a patient's urethra.

21. A method of facilitating visualization of a patient's prostate, the method comprising the steps of:
   providing apparatus comprising a catheter having a first inlet port and a first outlet port, a first lumen extending therebetween, and having a second inlet port and a second outlet port, a second lumen extending therebetween, the second outlet port disposed proximal of the first outlet port, and a disk-shaped bladder neck balloon comprising a proximally-directed flange and coupled to the first outlet port, the balloon expandable from a delivery configuration to a deployed configuration;
   advancing the apparatus through the patient's urethra until the balloon is disposed within the patient's bladder;
   injecting a fluid through the first inlet port, the first lumen, and the first outlet port to expand the balloon from the delivery configuration to the deployed configuration; and
   sealingly engaging an exterior surface of the balloon against a proximal portion of the patient's bladder to define an enclosed space.

22. The method of claim 21 further comprising injecting an echo-contrast agent into the enclosed space through the second inlet port, the second lumen, and the second outlet port to facilitate visualization of the patient's prostate.

23. The method of claim 21 further comprising:
   ultrasonically imaging a junction between the patient's bladder and the patient's prostate.

24. The method of claim 23, wherein the bladder neck balloon comprises a radiopaque material.

25. The method of claim 23 further comprising:
   performing brachytherapy on the patient's prostate.

26. The method of claim 21, wherein the catheter further comprises a third inlet port and a third outlet port, a third lumen extending therebetween, the third outlet port disposed distal of the first outlet port,
   the method further comprising emptying fluid from the patient's bladder through the third outlet port, the third lumen, and the third inlet port.

27. The method of claim 21 further comprising inserting a therapeutic agent or an interventional device into the patient's prostate through the second inlet port, the second lumen, and the second outlet port.

28. The method of claim 21, wherein the catheter further comprises a pressure channel, and wherein advancing the apparatus through the patient's urethra comprises injecting fluid into the pressure channel to stiffen the catheter.

29. The method of claim 21 further comprising providing a rigid tubular sleeve, wherein advancing the apparatus through the patient's urethra comprises advancing the apparatus with the rigid tubular sleeve removably disposed about the catheter.

30. The method of claim 29 further comprising removing the rigid tubular sleeve from the catheter.

31. Apparatus for facilitating visualization of a patient's prostate comprising:
   a catheter comprising a first inlet port and a first outlet port, a first lumen extending therebetween, and a second inlet port and a second outlet port, a second lumen extending therebetween, the second outlet port disposed proximal of the first outlet port; and a disk-shaped bladder neck balloon coupled to the first outlet port, the balloon expandable from a delivery configuration adapted for transurethral insertion, to a deployed configuration adapted for sealing engagement of an enclosed space within a proximal portion of the patient's bladder, wherein the balloon is fabricated from a plurality of bands of material, the plurality of bands varying each from another by a property chosen from the group consisting of stiffness, thickness, and elasticity.

32. The apparatus of claim 31, wherein the catheter further comprises a third inlet port and a third outlet port, a third lumen extending therebetween, the third outlet port disposed distal of the first outlet port.

33. The apparatus of claim 32, wherein the catheter further comprises a fourth inlet port and a fourth outlet port, a fourth lumen extending therebetween, the fourth outlet port disposed proximal of the second outlet port.

34. The apparatus of claim 31, wherein the catheter further comprises a third inlet port and a third outlet port, a third lumen extending therebetween, the third outlet port disposed proximal of the second outlet port.

35. The apparatus of claim 34, wherein the third outlet port is disposed between 3 cm and 5 cm proximal of the first outlet port.

36. The apparatus of claim 31, wherein the disk-shaped bladder neck balloon is concave towards the proximal end of the catheter in the deployed configuration.

37. The apparatus of claim 31, wherein the disk-shaped bladder neck balloon includes a proximally-directed flange.

38. The apparatus of claim 31 further comprising:
brachytherapy apparatus configured for delivery of radioactive seeds to the patient's prostate, wherein delivery of the seeds is facilitated by ultrasonic imaging of a junction of the patient's prostate and bladder.

39. The apparatus of claim 31, wherein the bladder neck balloon is fabricated from a material chosen from the group consisting of silastic and latex polyisoprene.

40. The apparatus of claim 31, wherein the bladder neck balloon is configured to expand nonuniformly to the deployed configuration.

41. The apparatus of claim 31, wherein the bladder neck balloon is configured to expand uniformly to the deployed configuration.

42. The apparatus of claim 31, wherein the catheter has a length of between 35 cm and 45 cm.

43. The apparatus of claim 31, wherein the bladder neck balloon has a diameter of between 4 cm and 5 cm.

44. The apparatus of claim 31, wherein an outer edge of the bladder neck balloon is offset relative to a center of the bladder neck balloon by a distance of between 1 and 3 cm.

45. The apparatus of claim 31 further comprising echo-contrast agent in communication with the second inlet port for delivery of the echo-contrast agent to the enclosed space.

46. The apparatus of claim 31, wherein the bladder neck balloon comprises a radiopaque material.

47. The apparatus of claim 31, wherein the catheter further comprises a pressure channel coupled to a pressure inlet port.

48. The apparatus of claim 31 further comprising a rigid tubular sleeve removably disposed about the catheter.

49. The apparatus of claim 48, wherein the sleeve has a natural curve adapted to match the curve of a patient's urethra.

50. The apparatus of claim 31, wherein the catheter has a natural curve adapted to match the curve of a patient's urethra.

51. A method of facilitating visualization of a patient's prostate, the method comprising the steps of:

providing apparatus comprising a catheter having a first inlet port and a first outlet port, a first lumen extending therebetween, and having a second inlet port and a second outlet port, a second lumen extending therebetween, the second outlet port disposed proximal of the first outlet port, and a disk-shaped bladder neck balloon coupled to the first outlet port, the balloon expandable from a delivery configuration to a deployed configuration, wherein the balloon is fabricated from a plurality of bands of material, the plurality of bands varying each from another by a property chosen from the group consisting of stiffness, thickness, and elasticity;

advancing the apparatus through the patient's urethra until the balloon is disposed within the patient's bladder;

injecting a fluid through the first inlet port, the first lumen, and the first outlet port to expand the balloon from the delivery configuration to the deployed configuration; and sealingly engaging an exterior surface of the balloon against a proximal portion of the patient's bladder to define an enclosed space.

52. The method of claim 51 further comprising injecting an echo-contrast agent into the enclosed space through the second inlet port, the second lumen, and the second outlet port to facilitate visualization of the patient's prostate.

53. The method of claim 51 further comprising:
ultrasonically imaging a junction between the patient's bladder and the patient's prostate.

54. The method of claim 53, wherein the bladder neck balloon comprises a radiopaque material.

55. The method of claim 53 further comprising:
performing brachytherapy on the patient's prostate.

56. The method of claim 51, wherein the catheter further comprises a third inlet port and a third outlet port, a third lumen extending therebetween, the third outlet port disposed distal of the first outlet port, the method further comprising emptying fluid from the patient's bladder through the third outlet port, the third lumen, and the third inlet port.

57. The method of claim 51 further comprising inserting a therapeutic agent or an interventional device into the patient's prostate through the second inlet port, the second lumen, and the second outlet port.

58. The method of claim 51, wherein the catheter further comprises a pressure channel, and wherein advancing the apparatus through the patient's urethra comprises injecting fluid into the pressure channel to stiffen the catheter.

59. The method of claim 51 further comprising providing a rigid tubular sleeve, wherein advancing the apparatus through the patient's urethra comprises advancing the apparatus with the rigid tubular sleeve removably disposed about the catheter.

60. The method of claim 59 further comprising removing the rigid tubular sleeve from the catheter.

* * * * *